United States Patent [19]

McVicker

[11] 4,318,826
[45] Mar. 9, 1982

[54] CARBONYLATION CATALYSTS

[75] Inventor: Gary B. McVicker, Westfield, N.J.

[73] Assignee: Exxon Research & Engineering Co., Florharm Park, N.J.

[21] Appl. No.: 139,152

[22] Filed: Apr. 11, 1980

Related U.S. Application Data

[60] Continuation of Ser. No. 17,717, Mar. 5, 1979, abandoned, which is a division of Ser. No. 799,589, May 23, 1977, abandoned, which is a continuation-in-part of Ser. No. 166,615, Jul. 27, 1971, abandoned, which is a continuation-in-part of Ser. No. 51,669, Jul. 1, 1970, abandoned.

[51] Int. Cl.$^3$ ............................................. B01J 31/24
[52] U.S. Cl. .................................. 252/431 P; 560/232
[58] Field of Search ............................. 252/473, 431 P

[56] References Cited

U.S. PATENT DOCUMENTS 3,769,329  10/1973  Paulik et al. ..................... 562/518 X
3,968,128   7/1976  McVicker ........................ 260/347.8
4,250,329   5/1979  McVicker ........................... 560/232

OTHER PUBLICATIONS

McVicker, Inorganic Chemistry, vol. 14, pp. 2087 to 2092 (1975).
McVicker et al, J. of the Chem. Soc., Chemical Communications, 1972, p. 972.
Hieber et al, Ztschr. f. anorgan. u. allgem, Chemie, vol. 314, pp. 125 to 143 (1962).
Hieber et al, Chem. Ber. vol. 94, pp. 1417–1425 (1961).

*Primary Examiner*—Richard A. Schwartz
*Attorney, Agent, or Firm*—Albert P. Halluin; Henry E. Naylor

[57] ABSTRACT

A carbonylation catalyst composition comprising a mixture of:
(a) $(C_4H_8O)_4Mg[Co(CO)_3P(C_4H_9)_3]_2$ or $(C_4H_8O)_4Mg[Rh(CO)_3P(C_4H_9)_3]_2$ and an organo iodine compound selected from the group consisting of $CH_3I$, $CH_2CH_3I$, and $C_6H_5I$.

2 Claims, No Drawings

CARBONYLATION CATALYSTS

CROSS-REFERENCE TO RELATED APPLICATIONS

This is a continuation, of appliction Ser. No. 17,717, filed Mar. 5, 1979 now abandoned, which is a Division of Ser. No. 799,589, filed May 23, 1977, now abandoned, which is a CIP of 166,615, filed July 27, 1971, now abandoned, which is a CIP of Ser. No. 51,669, filed July 1, 1970, now abandoned.

FIELD OF THE INVENTION

The present invention is directed to a carbonylation process for the preparation of carboxylic acid esters wherein carbon monoxide is contacted with at least one alcohol in the presence of a catalyst system having the general formula:

$$B_xM[Me'(CO)_a(L)_b]_2$$

and a cocatalyst comprising halogen containing compounds in a cocatalyst to catalyst molar ratio ranging from about 1 to about 16, wherein B is a Lewis base capable of coordinating with a Group IIA metal; Me is a Group IIA metal, preferably magnesium; Me' is a transition metal selected from the group consisting of metals of Groups VIB, VIIB and VIII of the Periodic Table of the Elements; L is a uni- or polydentate ligand or hydrocarbon capable of coordinating with the transition metal; x is a positive integer ranging from 1 to 4; a is a positive integer ranging from 1 to 5; b is an integer ranging from 0 to 4, with the proviso that the sum of a and b is 5 or less. A typical preferred catalyst system is represented by the general formula: $(C_4H_8O)_4Mg[Co(CO)_3P(C_4H_9)_3]_2$ and a cocatalyst comprising methyl iodide in cocatalyst to catalyst molar ratio of ranging from 1 to 4.

DESCRIPTION OF THE PRIOR ART

Carbonylation processes wherein alcohols, ethers, esters and halogen-containing compounds are contacted with carbon monoxide at high temperatures and pressures are known in the art. The catalysts which have been utilized in the prior art processes are generally Group VIII metals, e.g., cobalt, nickel and iron salts which under the carbonylation reaction conditions will be converted to carbonyl compounds.

In U.S. Pat. No. 2,650,646 there is disclosed a process for carbonylating methanol by contacting methanol with carbon monoxide in the presence of a nickel carbonyl compound and methyl iodide. This patent also indicates that the volatility of the nickel carbonyl and methyl iodide pose a problem to the skilled artisan. For example, it is known that catalyst loss due to volatility is a severe problem when employing any of the simple carbonyl derivatives of cobalt, nickel and iron.

In U.S. Pat. No. 2,710,878 a further problem in the process for the conversion of an alcohol to an organic acid in the presence of a catalyst system comprising a nickel or a cobalt salt and a halide cocatalyst is disclosed, i.e., the necessary high temperatures, pressures and acidic reaction mixtures cause extreme corrosion of the usual reactor equipment.

U.S. Pat. Nos. 2,898,366 and 2,898,367 disclose a process wherein lower aliphatic alcohols are reacted with carbon monoxide in the presence of a catalyst system comprising a nickel salt and iodine and/or hydrogen iodide at temperatures of at least 325° C. and pressures upwards of 3,000 psi.

U.S. Pat. No. 3,014,962 discloses a more active catalyst system wherein a chelating compound is added to the iron, cobalt and nickel salt catalyst and halogen containing cocatalyst of the prior art processes. This catalyst system produces carboxylic acids as the major product.

U.S. Pat. Nos. 2,734,193 and 3,505,408 describe carbonylation catalyst systems wherein the nickel or cobalt is in the anion of a complex salt. These systems, although useful in the hydroformylation of olefins, are not very active alcohol carbonylation catalysts.

The covalent nature of bonds between main group elements and transition metals has been well established by numerous chemical, structural, and spectroscopic investigations. Many compounds are known in which a main Group IVA or IIB metal is covalently bonded to a transition metal. Cases in which a transition metal is bonded to an element of main Group IIA or IIIA are, by contrast, few in number. Group IA transition metal compounds are known but are essentially ionic and are generally not isolatable and are handled as solutions in polar solvents.

It is generally found that the covalent nature of a main Group IIIA or main Group IVA metal bonded to a transition metal decreases as one moves from Group IVA to Group IIIA or ascends either respective group. This trend in covalent bonding is responsible for the failure of the early numbers of Group IIIA to form readily insoluble compounds with transition metals (the transition metal anion is the seat of reactivity and is readily attacked by electrophiles).

Group IIA-transition metal compounds have been described in two instances, but in both cases hereafter noted, the proposed composition and structure was incorrectly postulated. Von W. Hieber et al., *Zeitschrift fur anorganische und allgemeine Chemie*, pp. 125–143 (March, 1962) described the reaction of a dimeric manganese carbonyl complex with magnesium amalgam in the presence of tetrahydrofuran to give the bis-tetrahydrofuran adduct of a magnesium-manganese carbonyl complex. This product is not produced under the reaction conditions described; instead the tetrakis adduct is obtained in quantitative yield. Furthermore, Hieber et al, only teach a method for preparing the complex $(C_4H_8O)_2Mg[Mn(CO_4)P(C_6H_5)_3]_2$. The stability of this complex is largely due to the stabilizing effect of the phosphine ligand $P(C_6H_5)_3$. The ability of $P(C_6H_5)_3$ to impart thermal stability to carbonyl complexes is well documented in the literature.

Burlitch and Ulmer, *Journal of Organometallic Chemistry*, 19 pp. 21–23 (1969) described the preparation of halides of magnesium transition metal carbonyl complexes (transition metal carbonyl Grignard reagents) by the reaction of the transition metal carbonyl halide with magnesium in the presence of tetrahydrofuran. Burlitch and Ulmer did not isolate these products, but inferred that they existed by further reactions of the unisolated complex. The applicant has found that halide derivatives of magnesium-transition metal carbonyl complexes cannot be isolated, but, instead, if formed, immediately disproportionate to give bistransition metal derivatives of magnesium complexed with Lewis base molecules and magnesium halide.

Group IIA-transition metal compounds would be expected to be more ionic in nature than the corresponding IIB derivatives. A balance between covalent and ionic bonding contributions to the hetero metal-metal bond is needed to insure reasonable solubility in organic solvents. Hydrocarbon solubility is, of course, a necessity for use of the Group IIA-transition metal compound as a homogeneous catalyst for hydrogenation, polymerization, dimerization, carbonylation and hydroformylation reactions:

DISCOVERY OF THE INVENTION

It has been unexpectedly found that a transition metal carbonyl can be reacted with a metal chosen from Group IIA of the Periodic Table of the Elements in the presence of a Lewis base, to give novel compounds, wherein the transition metal is bonded to the Group IIA. This reaction is effected, preferably, by the reaction of an amalgam of the Group IIA metal with a dimeric transition metal carbonyl complex.

It has also been discovered that these novel compounds are effective catalysts for carbonylation reactions to produce acids, esters, ethers and acyl halides.

More particularly it has been discovered that these novel compounds provide an excellent catalyst system when used in combination with a halogen containing compound as a cocatalyst to produce carboxylic acid esters from alcohols.

SUMMARY OF THE INVENTION

One aspect of the present invention is directed to an improved carbonylation process comprising contacting a compound of the general formula R-X wherein R represents a hydrocarbyl radical and X represents a halogen, hydroxyl or bisulfide radical (SH) with carbon monoxide in the presence of a novel catalyst system, said novel catalyst system comprising a Group IIA metal-transition metal carbonyl catalyst wherein the transition metal is bonded to the Group IIA metal and a halogen containing cocatalyst, preferably an iodine-containing catalyst and more preferably an iodine containing compound selected from the group consisting of $I_2$, HI, and organo iodides such as $CH_3I$, $CH_3CH_2$) and $C_6H_5I$. An especially preferred iodine compound is $CH_3I$. Preferably X represents a hydroxyl radical and thus alcohols are the preferred carbonylation reactants.

Another aspect of the present invention is directed to an improved carbonylation process comprising contacting an olefinic compound and an alcohol with a carbon monoxide containing gas in the presence of a novel catalyst system, said novel catalyst system comprising a Group IIA metal-transition metal carbonyl catalyst wherein the transition metal is bonded to the Group IIA metal and having the general formula:

$$B_xMe(M)_2$$

wherein B is a Lewis base; x is an integer ranging from 1 to 4; Me is a Group IIA metal; and M is a transition metal carbonyl or substituted transition metal carbonyl complex.

The processes of the present invention provide an improved means for obtaining carboxylic acid esters and ethers. By use of the improved catalyst system of the instant invention, the following improvements are noted:

(1) Lower temperatures and pressures may be used.
(2) Either ethers or esters may be selectively produced by varying the ratio of the catalyst and cocatalyst.
(3) The catalyst system is non-volatile.
(4) The reaction mixtures are non-corrosive.

DESCRIPTION OF THE PREFERRED EMBODIMENTS

A preferred aspect of the present invention relates to a carbonylation process for the preparation of carboxylic acid esters which comprises contacting carbon monoxide with at least one alcohol at a temperature in the range from about 100° to about 200° C. and at a carbon monoxide partial pressure in the range from about 1000 to about 4000 psig in the presence of a catalyst system having the general formula:

$$B_x Me[Me'(CO)_a(L)_b]_2$$

and a cocatalyst comprising halogen containing compounds in a cocatalyst to catalyst molar ratio ranging from about 1 to about 16, wherein B is a Lewis base capable of coordinating with a Group IIA metal, Me' is a transition metal selected from the group consisting of metals of Groups VIB, VIIB and VIII of the Periodic Table of Elements, Me is a Group IIA metal, L is a uni- or polydentate ligand or hydrocarbon capable of coordinating with said transition metal; x is a positive integer ranging from 1 to 4; a is a positive integer ranging from 1 to 5 and b is an integer ranging from 0 to 4, with the proviso that the sum of a and b is 5 or less. The catalyst is preferably an iodine containing compound selected from the group consisting of $I_2$, HI, and organo iodides such as $CH_3I$, $CH_3CH_2I$ and $C_6H_5I$. In especially preferred iodine compound is $CH_3I$.

This process is capable of producing carboxylic acid esters in high yield and good selectivity at low temperatures and pressures. These advantages are attributed to the use of the novel catalyst compounds wherein the transition metal is bonded to the Group IIA metal.

The alcohols used as the preferred starting materials in the carbonylation process include the hydrocarbyl alcohols such as alkanols and aralkanols which contain from 1 to about 20 carbon atoms. Preferred alcohols include methanol, ethanol, propanol, isopropanol, butanol, and mixtures thereof, methanol being particularly preferred.

In general, the carbonyl ion process of the instant invention will take place at a temperature of from 100° to 400° C. and at a carbon monoxide partial pressure ranging from about 500 to about 10,000 psig, depending on the preponderance of products desired, i.e., ethers or esters.

The alcohol reactant may be contacted with the carbon monoxide containing gas neat or dissolved in a solvent. Solvents which can be utilized in the process of the instant invention include benzene, toluene, tetrahydrofuran, ethyl ether, etc.

It is obvious that the carbon monoxide does not have to be added to the reaction product in pure form. It may be combined with various inert gases. For example, an especially economical source of carbon monoxide, i.e., from partial combustion or steam reforming processes, will contain $CO_2$ and hydrogen as well as carbon monoxide. This mixture can be used in the process of the instant invention.

The molar ratio of the catalyst system to the alcohol reactant may vary from 0.0001 to 0.1, preferably 0.001 to 0.1. The molar ratio of co-catalyst to catalyst may vary from 1 to 100, preferably from 1 to 4, depending on the preponderance of product, i.e., ether or ester if one wishes to obtain as explained below.

The reaction time will be apparent to the skilled artisan and he may choose his reaction time based on the temperatures and pressures utilized.

The instant process is capable of being run batchwise or continuously. The process of the instant invention will usually be run in reactors known to the skilled artisan and includes, because of the oxygen sensitivity of the catalyst system of the instant invention, provisions for the exclusion of oxygen. It is noted that special reactor lines are not needed in the process of the instant invention because of the relatively low temperatures and pressures utilized and the noncorrosive nature of the catalyst.

In practicing the process of the instant invention, a hydrocarbyl alkanol having from 1 to 20 carbon atoms is contacted with carbon monoxide in the presence of the novel catalyst system at an elevated temperature and pressure for a time sufficient to convert at least some of the alcohol to a carbonylated product. The composition of the final reaction product, i.e., ester or ether, is controlled by varying the reaction conditions including the cocatalyst to catalyst ratio. It has been discovered that ester formation is favored by increased carbon monoxide partial pressures and low cocatalyst to catalyst ratios, whereas ether formation is favored by relatively high ratios of cocatalyst to catalyst, high temperatures and low carbon monoxide pressures.

For example, a carbon monoxide pressure ranging from about 500 to 1000 psig favors ether formation, whereas carbon monoxide pressures ranging from 1000 to 4000 psig favors ester formation. A temperature ranging from 200 to 400° C. favors ether formation whereas temperatures ranging from 100° to 200° C. favors ester formation. A cocatalyst to catalyst molar ratio range of from 16 to 100 favors ether formation, whereas a cocatalyst to catalyst molar ratio of from 1 to 16 favors ester formation.

It will be noted that the process of the instant invention is capable of being operated at low temperatures and pressures compared to the prior art processes and therefore represents a significant advantage. Also, increased selectivity to ester (when desirable), high catalyst stability, and noncorrosive reaction mixture are important improvements of the present process over the known-in-the-art carbonylation processes.

The process of the instant invention is also applicable to the production of unsymmetrical ethers and esters. For example, a mixture of methanol and isopropanol when reacted under conditions to yield ethers will give the following products: dimethyl ether, diisopropyl ether and methyl isopropyl ether. Similar results are obtained when the reaction is run under conditions so that an ester product will be dominant, i.e., methyl acetate, isopropyl acetate, and small amounts of methyl propionate and isopropyl propionate will be produced. In general, in a process for producing esters, the lower alcohol will preferably form the acyl function. Of course, the reaction conditions can be adjusted so that mixtures comprising both esters and ethers are formed at once. The formation of unsymmetrical lower alkyl ethers is especially important since these products have utility as octane improvers for gasolines.

The Novel Catalyst Compounds

The novel catalyst compounds used in the carbonylation process of the present invention are preferably those represented by the general formula:

$$B_x Me[Me'(CO)_a(L)_b]_2$$

B is a Lewis base capable of coordinating with a Group IIA metal, such as magnesium, through a lone pair of electrons thereby stabilizing the Group IIA metal-transition metal complexes. The Lewis base is preferably a member selected from the group consisting of:
1. Organic nitrogen bases;
2. Ethers; and
3. Ketones. Me is a Group IIA metal, preferably magnesium; Me' is a transition metal selected from the group consisting of Groups VIB, VIIB and VIII metals (examples of the useful transition metals include molybdenum, tungsten, cobalt, nickel, ruthenium, rhodium, palladium, osmium, iridium and platinum, cobalt being the most preferred); L is a uni- or polydentate ligand capable of coordinating with the transition metal or a hydrocarbon residue; x is a positive integer ranging from 1 to 4; a is a positive integer ranging from 1 to 5; b is an integer ranging from 0 to 4, with the proviso that the sum of a and b is 5 or less.

The organic nitrogen bases (B) useful as Lewis bases to coordinate with the Group IIA metal and selected from the group consisting of:

(a) monofunctional nitrogenous bases represented by the general formulae:

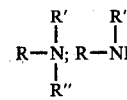

R—NH$_2$; and NH$_3$ wherein R, R' and R" are hydrocarbyl radicals independently selected from the group consisting of C$_1$ to C$_{10}$ alkyl, C$_3$ to C$_{10}$ cycloalkyl, C$_6$ to C$_{10}$ aryl and C$_7$ to C$_{10}$ alkaryl and aralkyl radicals;

(b) polyfunctional nitrogenous bases represented by the general formula:

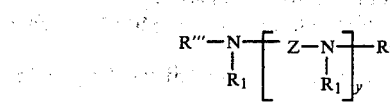

wherein R" and R$^{iv}$ are selected from the group consisting of hydrogen and C$_1$ to C$_{10}$ hydrocarbyl radicals, R$_1$ is selected from the group consisting of hydrogen and C$_1$ to C$_4$ alkyl radicals, Z is selected from the group consisting of radicals represented by the general formulae:

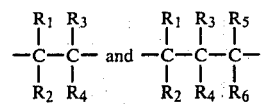

wherein R$_1$, R$_2$, R$_3$, R$_4$, R$_5$ and R$_6$ are independently selected from the group consisting of hydrogen and C$_1$ to C₄ alkyl radicals and y is a positive integer ranging from 1 to 3; and (c) Heteroring nitrogenous bases selected from the group consisting of piperazine, pyrrolidine, pyridine and substituted pyridines of the formula:

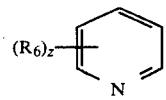

wherein $R_6$ is a $C_1$ to $C_{10}$ hydrocarbyl and z is an integer from 0 to 5.

Preferred examples of organic nitrogen bases which are within the above description include: monofunctional nitrogenous bases:
Ammonia
Methylamine
Dimethylamine
Trimethylamine
Triethylamine
Methyl diethylamine
Pyridine
N-decyl pyridine
Aniline
Bifunctional nitrogenous bases:
2,2'-bipyridyl
1,10-phenanthroline
Ethylene diamine
tetramethylethylenediamine
1,3-propylene diamine
Tetrafunctional nitrogenous bases:

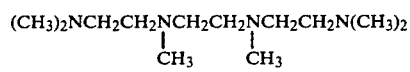

Hexamethyltriethylenetetraamine
Triethylenctetramine

The ethers useful as Lewis bases (b) to coordinate with the Group IIA metal are selected from the group consisting of:

(a) monofunctional ethers represented by the general formula:

wherein R and R' are hydrocarbyl radicals independently selected from the group consisting of $C_1$ to $C_{10}$ alkyl, $C_3$ to $C_{10}$ cycloalkyl, $C_6$ to $C_{10}$, $C_7$ to $C_{10}$ alkaryl and aralkyl radicals;

(b) polyfunctional ethers represented by the general formulae:

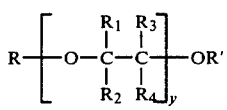

and

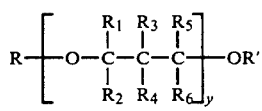

wherein $R_1$, $R_2$, $R_3$, $R_4$, $R_5$ and $R_6$ are independently selected from the group consisting of hydrogen and $C_1$ to $C_4$ alkyl radicals, R and R' are hydrocarbyl radicals independently selected from the group consisting of $C_1$ to $C_{10}$ alkyl, $C_3$ to $C_{10}$ cycloalkyl, $C_6$ to $C_{10}$ aryl and $C_7$ to $C_{10}$ alkaryl and aralkyl radicals and y is a positive integer of from 1 to 3; and (c) cyclic ethers selected from the group consisting of tetrahydrofuran and dioxane.

Examples of mono-, bi- and tetrafunctional oxygenated ethers which can coordinate to Group IIA metals, e.g., magnesium through a lone pair of electrons thereby stabilizing the Group IIA metal-transition metal complexes are listed below.

Monofunctional ethers

Tetrahydrofuran
Tetrahydropyran
Dioxane
Diethyl ether
Dipropyl ether
Methyl ethyl ether
Dicyclohexyl ether
Diphenyl ether
Methylphenyl ether Difunctional ethers CH₃OCH₂CH₂OCH₃(glyme)
CH₃CH₂OCH₂CH₂OCH₂CH₂(1,2-di-ethoxyethane)
C₃H₇OCH₂CH₂OCh₂CH₃(1-propoxy-2-ethoxyethane)
C₆H₅OCH₂CH₂OC₆H₅(1,2-diphenoxy-ethane)

Tetrafunctional ethers

CH₃OCH₂CH₂OCH₂CH₂OCH₂CH₂OCH₃(triglyme)

Ketones useful as Lewis bases (B) to coordinate with the Group IIA metal are represented by the general formula:

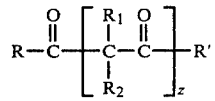

wherein R and R' are hydrocarbyl radicals independently selected from the group consisting of $C_1$ to $C_{10}$ alkyl, $C_3$ to $C_{10}$ cycloalkyl, $C_6$ to $C_{10}$ aryl and $C_7$ to $C_{10}$ alkaryl and aralkyl radicals, $R_1$ and $R_2$ are independently selected from the group consisting of hydrogen and $C_1$ to $C_4$ alkyl radicals and z is an integer of from 0 to 3.

Examples of useful ketones are listed below:
Acetone
Methyl ethyl ketone
Dicyclohexyl ketone
Methyl cyclohexyl ketone
Diphenyl ketone
Cyclohexanone
Methyl phenyl ketone
Acetylacetone
1,2-cyclohexandione
1,3-cyclohexandione and
2,4,6,8-n-nonatetraone.

L is preferably selected from compounds of the group having the following general formulae:

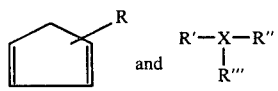 and R'—X—R''
        |
       R''' wherein R, R', R'' and R''' are hydrocarbyl radicals independently selected from the group consisting of hydrogen, $C_1$ to $C_{20}$ alkyl, $C_3$ to $C_{20}$ cycloalkyl, $C_6$ to $C_{20}$ aryl and $C_7$ to $C_{20}$ aralkyl and alkaryl radicals and X is a member selected from the group consisting of N, P, As and Sb, with P being preferred.

Thus, compounds within the scope of this definition include:

Cyclopentadiene
Methyl cyclopentadiene
Ethyl cyclopentadiene
Butyl cyclopentadiene
Phosphine
Trimethyl phosphine
Triethyl phosphine
Tributyl phosphine
Methyl diphenyl phosphine
Triphenyl phosphine
Butyl diphenyl phosphine
Triethylamine
Triethylarsine, and
Triethylstibine.

L may also represent more than one ligand independently selected from the above group. For example, in the compound $[C_4H_8O]_4Mg[Mo(CO)_2(PCH_3(C_6H_5)_2C_5H_5]_2$ wherein a would equal 2, and L would equal methyl diphenyl phosphine and cyclopentadiene.

The above-mentioned novel compounds can be prepared by any of four methods:

1. A slight excess of $MeX_2$ (wherein Me is a Group IIA metal and X is Cl, Br or I, preferably Cl or Br) dissolved in tetrahydrofuran (THF) can be added to the Na derivative of the transition metal carbonyl complex, with agitation. After the reaction is complete, the crude reaction mixture is filtered to remove the insoluble NaX formed. The filtrate is concentrated with reduced pressure and the magnesium transition metal compound is precipitated by adding n-pentane. The solid product is purified by recrystallization from benzene. Examples of some sodium derivatives of transition carbonyl complexes include:

Na⊕ Fe(CO)$_2$(C$_5$H$_5$)⊖
Na⊕ Mo(CO)$_3$(C$_5$H$_5$)⊖
Na⊕ Co(CO)$_4$⊖
Na⊕ Co(CO)$_3$(P(nC$_4$H$_9$)$_3$))⊖

Examples of reaction pathways:

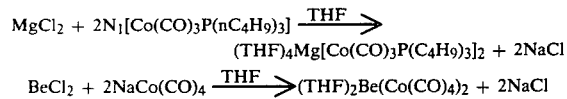

(2) A solution of a transition metal carbonyl derivative of Hg is reacted with the Group IIA metal. The crude reaction mixture is filtered to remove the free mercury formed by the metal exchange reaction. The magnesium transition metal compound is isolated from the filtrate as in (1) above. Examples of some Hg derivatives of transition metal carbonyl complexes include:

Hg(Fe(CO)$_2$C$_5$H$_5$)$_2$
Hg(Co(CO)$_4$)$_2$
Hg(Co(CO)$_3$P(C$_6$H$_5$)$_3$)$_2$
Hg(Mo(CO)$_3$C$_5$H$_5$)$_2$

Typical reaction pathway:

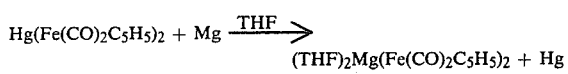

(3) The same procedure as in (2), except that a transition metal carbonyl halide compound is used instead of the mercury derivative. The Group IIA halide formed is removed by filtration. Examples of some transition metal carbonyl halides include:

(C$_5$H$_5$) Fe(CO)$_2$I, (C$_5$H$_5$)Fe(CO)$_2$Br
(C$_5$H$_5$) Mo(CO)$_3$I
(C$_5$H$_5$) Mo(P(nC$_4$H$_9$)$_3$)(CO)$_2$I
(C$_5$H$_5$)Ni(CO)I
((C$_6$H$_5$)$_3$Rh(CO)Cl
(CO)$_5$MnBr

Typical reaction pathway:

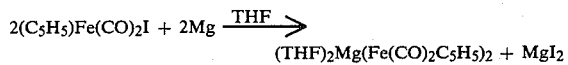

(4) An amalgam of the Group IIA metal is reacted with a dimeric metal carbonyl complex yielding the above mentioned novel compounds. Examples of some dimeric metal carbonyl complexes include:

(Fe(CO)$_2$(C$_5$H$_5$))$_2$
(Mo(CO)$_3$(C$_5$H$_5$))$_2$
((C$_5$H$_5$)Ni(CO))$_2$
Co$_2$(CO)$_8$
Co$_2$(CO)$_6$(P(nC$_4$H$_9$)$_3$)$_2$
Mn$_2$(CO)$_{10}$
(W(CO)$_3$C$_5$H$_5$)$_2$

Typical reaction pathway:

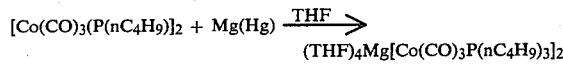

All of the above procedures are carried out under an inert atmosphere, generally nitrogen. The reaction temperature range varies from −40° C. to 300° C., preferably between 0° C. and 120° C., and most preferably between room temperature and 100° C.

The reaction of the Group IIA metal (and also the halide or amalgam as shown above) and the transition metal carbonyl complex normally takes place in a solvent. Inert solvents such as benzene, toluene, n-pentane, etc., can be used as long as there is also present enough Lewis base such as pyridine, tetrahydrofuran, etc., to coordinate with the Group IIA metal, as noted above. Preferably, the reaction is carried out in the presence of a substantial excess of the Lewis base, and if the reactants are soluble in the Lewis base, the solvent can consist entirely of the Lewis base. It should be noted that the solubility of the Group IIA-transition metal carbonyl complex in hydrocarbon solvents is dependent on the nature of the Lewis base adduct. For example, in benzene the solubility of the Lewis acid adducts increase in the following order: tetrahydrofuran, pyridine, and tetramethyldiethylenediamine.

The molar ratio of Group IIA metal and transition metal carbonyl complex is preferably greater than 1, since traces of oxygen will cause oxidation of the Group IIA-transition metal carbonyl complex according to the following reaction:

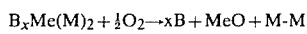

wherein the symbols have the meanings ascribed previously.

If the Group IIA metal is in excess, it will convert the transition metal carbonyl dimer back to the desired product according to the following reaction:

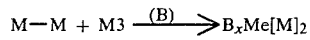

The MeO is easily separable since it will usually be a filterable solid. Also, if the transition metal carbonyl complex is in excess, the unreacted portion will be difficult to remove from the desired Group IIA-transition metal carbonyl compound.

For the above reasons, the mole ratio of Group IIA metal to transition metal usually ranges from 1 to 100 with a range of 1.1 to 10 preferred, and 1.1 to 3.3 specially preferred. It should be noted that if one does not intend to isolate the product, or does not find the economics, of separating the desired products from the reactants unattractive, lower ratios may be used.

The novel compounds described herein may be used as a catalyst in a variety of chemical processes in addition to the carbonylation process. For example, unsaturated organic compounds can be hydrogenated to give the corresponding saturated derivatives. These catalysts are also useful for hydroformylation reactions wherein an alkene is reacted with carbon monoxide and hydrogen to form aldehydes and alcohols. Excellent selectivity has been shown by the tetrakis tetrahydrofuran adduct of a magnesium-dicobalt hexacarbonyl bismethyldiphenylphosphine complex in the conversion of 1-hexene to heptaldehydes. The conversion was >99% with a selectivity of 87%. This conversion is run at elevated pressures, preferably from 1,500 to 3,000 psi. Reaction temperatures will range from 50° C. to 200° C., with a range of 100° C. to 150° C. preferred. Ratio of $H_2$ to CO used will vary with reaction conditions; preferably a 1 to 1 ratio is maintained. The catalyst concentration will range from 0.01 to 20% based on the weight feed, with 0.05 to 10% preferred.

The novel compounds described herein have also shown utility in the preparation of cyclic dimers and trimers of butadiene. In particular, cyclododecatriene may be produced by the trimerization of butadiene.

The above uses are in addition to the carbonylation of alkanols to carboxylic acid esters by use of the novel catalysts described above.

Reactions which utilize the novel catalyst will usually be run in the liquid phase; i.e., one advantageous characteristics of the catalyst of this invention is that its solubility in organic solvents can be varied by the proper choice of Lewis base adduct, thereby allowing the skilled artisan to design a homogeneous or heterogeneous catalyst system. The reactions which utilize the novel catalyst will be run at temperatures ranging from $-50°$ C. to 500° C. and pressures ranging from subatmospheric to superatmospheric, according to the specific reaction. The proper temperatures and pressure conditions will be apparent to one skilled in the art. In a like manner, the reaction times and the catalyst concentrations will vary according to the specific reaction, and will also be apparent to the skilled artist.

The following examples serve to more fully describe the manner of making and using the above-described invention, as well as to set forth the best modes contemplated for carrying out various aspects of the invention. It is understood that these examples in no way serve to limit the true scope of this invention, but rather, are presented for illustrative purposes.

Preparation of the Novel Catalyst

In the preparation of the novel catalyst, all reactions were carried out under a nitrogen atmosphere.

EXAMPLE A

Preparation of $[C_4H_8O]_2Mg[Fe(CO)_2C_5H_5]_2$

Method (1)

0.2 gms. $MgBr_2$ dissolved in 15 mls. of tetrahydrofuran was added dropwise to a solution of 0.4 gms. $Na[Fe(CO)_2C_5H_5]$ in 30 ml. of tetrahydrofuran, in a 100 ml. flask equipped with a magnetic stirrer. The $NaFe(CO)_2C_5H_5$ had been prepared by the reductive cleavage of $[C_5H_5Fe(CO)_2]_2$ with 1% sodium amalgam. This mixture was allowed to stir at room temperature for 24 hours. The crude reaction mixture was filtered and reduced pressure to remove the insoluble salts formed during the reaction. The filtrate was concentrated with reduced pressure. The concentrate was slowly poured into n-pentane which affected the precipitation of a yellow-orange solid. The crude product was recrystallized several times from benzene and vacuum dried. The pure solid is a bright yellow solid and is extremely air sensitive. Upon atmospheric exposure the magnesium-transition metal compound is quantitatively oxidized to $[C_5H_5Fe(CO)_2]_2$ and MgO. The stoichiometry of the complex was established by nmr and elemental analyses. The composition of all of the following novel products were determined by a combination of nmr and elemental analysis.

Calculated for $[C_4H_8O]_2Mg[Fe(CO)_2C_5H_5]_2$: 50.5% C, 4.97% H, 4.59% Mg, 21.6% Fe and a molecular weight of 522.

Found for reaction product: 46.7% C, 4.83% H, 4.64% Mg, 22.5% Fe and a molecular weight of 528 benzene.

Elemental analyses, molecular weight and color data for the novel catalyst compounds synthesized in this example and following examples are given in Table I.

It should be noted that the halide products postulated by Burlich and Ulmer were not produced.

TABLE I
ANALYTICAL DATA, MOLECULAR WEIGHTS[a] AND COLORS

| Compound | Color | Calculated % | | | | | |
| --- | --- | --- | --- | --- | --- | --- | --- |
| | | C | H | Mg | Me[1] | P | N |
| $(THF)_2Mg(Fe(CO)_2C_5H_5)_2$ | Yellow | 50.5 | 4.97 | 4.59 | 21.6 | — | — |
| $(Pyridine)_2Mg[Fe(CO)_2C_5H_5]_2$ | Yellow Light | 53.6 | 3.74 | 4.54 | 20.8 | — | 5.24 |
| $(THF)_4Mg[Mo(CO)_2PCH_3(C_6H_5)_2C_5H_5]_2$ | Yellow | 58.6 | 5.83 | 2.10 | 16.8 | 5.41 | — |
| $(THF)_4Mg[Mo(CO)_2P(C_4H_9)_3C_5H_5]_2$ | Yellow | 56.4 | 8.35 | 2.11 | 16.7 | 5.39 | — |

TABLE I-continued
ANALYTICAL DATA, MOLECULAR WEIGHTS[a] AND COLORS

| | | | | | | | |
|---|---|---|---|---|---|---|---|
| (Pyridine)$_4$Mg[Co(CO)$_4$]$_2$ | Yellow | 49.3 | 2.96 | 3.42 | 17.3 | — | 8.22 |
| (THF)$_4$Mg[Co(CO)$_3$PCH$_3$(C$_6$H$_5$)$_2$]$_2$ | Yellow | 57.6 | 5.83 | 2.40 | 11.8 | 6.20 | — |
| (THF)$_4$Mg[Co(CO)$_3$P(C$_4$H$_9$)$_3$]$_2$ | Yellow Green | 55.2 | 8.60 | 2.43 | 11.8 | 6.20 | — |
| (Pyridine)$_4$Mg[Co(CO)$_3$PCH$_3$(C$_6$H$_5$)$_2$]$_2$ | Yellow | 60.6 | 4.48 | 2.38 | 11.6 | 5.99 | 5.46 |
| (TMEDA)$_2$Mg[Co(CO)$_3$PCH$_3$(C$_6$H$_5$)$_2$]$_2$ | Yellow | 56.1 | 6.15 | 2.58 | 12.5 | — | — |
| (THF)$_4$Mg(Mn(CO)$_5$)$_2$ | Yellow | 44.5 | 4.56 | 3.46 | 15.7 | — | — |
| (THF)$_4$Mg[Mn(CO)$_4$PCH$_3$(C$_6$H$_5$)$_2$]$_2$ | Yellow | 57.4 | 5.54 | 2.32 | 10.5 | 5.94 | — |
| (Pyridine)$_4$Mg[Mn(CO)$_5$]$_2$ | Light Green | 49.3 | 2.94 | 3.29 | 15.1 | — | 7.67 |

| | Found % | | | | | | Molecular Weight | |
|---|---|---|---|---|---|---|---|---|
| | C | B | Mg | Me' | P | N | Calc. | Found |
| (THF)$_2$Mg(Fe(CO)$_2$C$_5$H$_5$)$_2$ | 46.7 | 4.83 | 4.64 | 22.5 | — | — | 522 | 228 |
| (Pyridine)$_2$Mg[Fe(CO)$_2$C$_5$H$_5$]$_2$ | 54.9 | 5.16 | 4.82 | 17.7 | — | 5.76 | 536 | 498 |
| (THF)$_4$Mo(CO)$_2$PCH$_3$(C$_6$H$_5$)$_2$C$_5$H$_5$]$_2$ | 58.3 | 5.61 | 3.09 | 17.4 | 6.25 | — | — | — |
| (THF)$_4$Mg[Mo(CO)$_2$P(C$_4$H$_9$)$_3$C$_5$H$_5$]$_2$ | 55.9 | 8.37 | 2.37 | 18.1 | 5.51 | — | 1150 | 599 |
| (Pyridine)$_4$Mg[Co(CO)$_4$]$_2$ | 49.4 | 3.26 | 2.91 | 17.1 | — | 7.79 | 682 | 665 |
| (THF)$_4$Mg[Co(CO)$_3$PCH$_3$(C$_6$H$_5$)$_2$]$_2$ | 55.9 | 6.01 | 2.36 | 11.1 | 6.26 | — | — | — |
| (THF)$_4$Mg[Co(CO)$_3$P(C$_4$H$_9$)$_3$]$_2$ | 54.6 | 8.74 | 2.45 | 11.4 | 5.99 | — | 1002 | 310 |
| (Pyridine)$_4$Mg[Co(CO)$_3$PCH$_3$(C$_6$H$_5$)$_2$]$_2$ | 58.6 | 4.51 | 2.51 | 11.7 | 5.69 | 5.41 | — | — |
| (TMEDA)$_2$Mg[Co(CO)$_3$PCH$_3$(C$_6$H$_5$)$_2$]$_2$ | 53.5 | 6.14 | 2.66 | 12.9 | — | — | — | — |
| (THF)$_4$Mg(Mn(CO)$_5$)$_2$ | 43.7 | 5.26 | 3.91 | 13.6 | — | — | — | — |
| (THF)$_4$Mg[Mn(CO)$_4$PCH$_3$(C$_6$H$_5$)$_2$]$_2$ | 56.6 | 6.01 | 2.55 | 9.79 | 6.19 | — | — | — |
| (Pyridine)$_4$Mg[Mn(CO)$_5$]$_2$ | 47.6 | 3.11 | 2.91 | 14.9 | — | 7.72 | — | — |

[a]Molecular weights were determined cryoscopically employing benzene solutions.

Method (2)

A solution containing 5.5 gm of H$_6$[Fa(CO)$_2$C$_5$H$_5$]$_2$ in 75 ml of tetrahydrofuran was added to a heavy walled reaction tube (equipped with a teflon vacuum stopcock) containing 0.5 gm of 200 mesh magnesium metal. The metal and reaction tube had previously been flamed out under a vacuum of 10$^{-4}$ mm. The reaction tube was sealed under vacuum and placed in an oil bath held at 85° C. After 24 hours the tube was broken and the contents filtered. The filtrate was concentrated with reduced pressure. The concentrate was poured into n-pentane which caused the precipitation of a yellow solid. The solid was collected and washed several times with a 25:75 mixture of benzene and n-pentane to remove any unreacted Hg[Fe(CO)$_2$C$_5$H$_5$]$_2$. The final purification procedure was recrystallization from benzene. The yield was 4.2 gm of [C$_4$H$_8$O]$_2$Mg[Fe(CO)$_2$C$_5$H$_5$]$_2$.

Method (3)

1.0 gm of magnesium powder (200 mesh) was placed in a heavy wall reaction tube. The tube and its contents were flamed out at 10$^{-4}$ mm. A solution of 6.0 gm of C$_5$H$_5$Fe(CO)$_2$I in 75 ml. of tetrahydrofuran was placed in the reaction tube. After a short induction period the reaction became exothermic enough to warm tetrahydrofuran to its reflux point. The initial red solution quickly turned dark yellow and the reaction appeared complete in 15 or 20 minutes. The crude reaction mixture was filtered. MgI$_2$ was collected on the filter and discarded. The filtrate was concentrated with reduced pressure. The concentrate was flooded with n-pentane causing the immediate precipitation of a yellow solid. The crude reaction product was collected and washed with a 50:50 mixture of n-pentane-ether to remove any unreacted C$_5$H$_5$Fe(CO)$_2$I. The remaining yellow solid was then recrystallized several times from benzene. The yield was very nearly quantitative.

Method (4)

In a 250 ml., 1-neck, round bottom flask 50 gm of mercury and 0.6 gm of 200 mesh magnesium powder were rapidly stirred to form the amalgam. The amalgam was allowed to cool to room temperature. To the amalgam was added a solution containing 5.0 gm of [C$_5$H$_5$Fe(CO)$_2$]$_2$ in 75 ml. of tetrahydrofuran. The resulting solution was deep red. The flask was stoppered and the mixture was stirred vigorously. After 18 hours the solution had become a yellow-green. The reaction mixture was filtered to free it from the amalgam. The filtrate was concentrated with reduced pressure to approximately 25 ml. The concentrated tetrahydrofuran solution was flooded with n-pentane, yielding a yellow solid. The yellow solid was recrystallized from benzene and vacuum dried. The yield was 7.2 gm of [C$_4$H$_8$O]$_2$Mg[Fe(CO)$_2$C$_5$H$_5$]$_2$.

EXAMPLE B

Preparation of (C$_5$H$_5$N)$_2$Mg[Fe(CO)$_2$C$_5$H$_5$]$_2$

In a 250 ml., 1-neck round bottom flask an amalgam consisting of 50 gm of mercury and 0.6 gm of powdered magnesium (200 mesh) was prepared. A solution containing 6.7 gm of pyridine in 125 ml. of benzene was added to the flask. To the benzene-pyridine solution was added 5.0 gm of [C$_5$H$_5$Fe(CO)$_2$]$_2$. The resultant solution was deep red. After 18 hours the solution had become a reddish-yellow with a considerable amount of a yellow solid suspended in the solution. The reaction mixture was filtered and an orange-yellow solid was collected. The collected solid was taken up in benzene and filtered to free it of magnesium amalgam. The filtrate was concentrated with reduced pressure. The concentrate was flooded with n-pentane, knocking out of solution a bright yellow solid. The solid was recrystallized from benzene and then vacuum dried. The yield was nearly quantitative. The bright yellow solid is air sensitive and is quantitatively oxidized to [C$_5$H$_5$Fe(CO)$_2$]$_2$ and MgO upon exposure to the air. The stoichiometry of the complex was established by nmr measurements and elemental analysis.

EXAMPLE C

Preparation of $(C_4H_8O)_4Mg[Mo(CO)_3C_5H_5]_2$

This compound was prepared by a method similar to that used in the preparation of $[C_4H_8O]_2Mg[Fe(CO)_2C_5H_5]_2$ described in Method 3 of Example A. $C_5H_5Mo(CO)_3I$ was prepared by cleaving the molybdenum-molybdenum bond of $[Mo(CO)_3C_5H_5]_2$ with $I_2$ in tetrahydrofuran solution. The magnesium-molybdenum compound is white and is only sparingly soluble in tetrahydrofuran. The stoichiometry of the compound $(C_4H_8O)_4Mg[Mo(CO)_3C_5H_5]_2$ was established by nmr measurements (solutions in d-acetonitrile) and elemental analysis. The same product was also prepared by cleaving $(Mo(CO)_3C_5H_5)_2$ with magnesium amalgam in tetrahydrofuran solution.

EXAMPLE D

Preparation of $(C_5H_5N)_4Mg[Mo(CO)_3C_5H_5]_2$

This compound was prepared by a method similar to that used in the preparation of the pyridine adduct, $(C_5H_5N)_2Mg[Fe(CO)_2C_5H_5]_2$, described in Example B above. The molybdenum cyclopentadienyl tricarbonyl dimer, $[C_5H_5Mo(CO)_3]_2$, was cleaved with magnesium amalgam in benzene solution in the presence of excess pyridine. The solubility of $(C_5H_5N)_4Mg[Mo(CO)_3C_5H_5]_2$ in benzene was found to be somewhat greater than the tetrakis tetrahydrofuran adduct. The pure solid is a light green. The stoichiometry of the compound was determined by nmr measurements upon d-acetonitrile solutions.

EXAMPLE E

Preparation of $(C_4H_8O)_4Mg[Mo(CO)_2(PCH_3(C_6H_5)_2)C_5H_5]_2$ 0.2 gm of magnesium powder (200 mesh) was flamed out in a heavy walled reaction tube (equipped with a teflon stopcock) under a vacuum of $10^{-4}$ mm. A solution containing 4.0 gm of $C_5H_5Mo(CO)_2(CH_3P(C_6H_5)_2)I$ (prepared by reacting equimolar quantities of $C_5H_5Mo(CO)_3I$ and $CH_3P(C_6H_5)_2$ in benzene solution) in 25 ml. of tetrahydrofuran was added to the reaction tube. The stopcock was closed and the tube was placed in an oil bath held at 50° C. to 60° C. After 18 hours the bulk of the magnesium powder had been consumed and an off-white solid had come out of solution. The reaction mixture was filtered leaving $MgI_2$ on the frit. The filtrate was concentrated with reduced pressure. A yellow solid was obtained by flooding the tetrahydrofuran concentrate with n-pentane. This solid was washed with a 50:50 mixture of benzene and n-pentane to remove any unreacted starting material. Nmr and elemental analysis have shown this compound to be the tetrakis tetrahydrofuran adduct. The tetrakis tetrahydrofuran adduct was also obtained in good yield by substituting a magnesium amalgam for the magnesium powder. The amalgam reaction could be carried out at room temperature.

EXAMPLE F

Preparation of $(C_4H_8O)_4Mg[Co(CO)_4]_2$

This compound was prepared by cleaving the cobalt-cobalt bond in $Co_2(CO)_8$ with magnesium amalgam in tetrahydrofuran solution. The dark yellow product is extremely air sensitive and is nearly insoluble in all common organic solvents. The air oxidation products are MgO and $Co_2(CO)_8$. The compound's insolubility would not allow a recrystallization, so purification was effected by repeated washings with a 50:50 tetrahydrofuran-n-pentane mixture. The washed solid was extracted with tetrahydrofuran yielding a dark yellow solution (solubility ca. 1 gm/l). A dark yellow solid was isolated by adding n-pentane to the saturated tetrahydrofuran solution. Infrared measurements showed the compound to be free of impurities.

EXAMPLE G

Preparation of $[(C_5H_5N)_4Mg[Co(CO)_4]_2$

This compound was prepared by cleaving $Co_2(CO)_8$ with magnesium amalgam in the presence of excess pyridine in benzene solution. The compound exhibits good solubility in hydrocarbon solvents and was recrystallized from benzene. Elemental analyses were in good agreement with the tetrakis pyridine formulation. The analytically pure compound is light yellow. The compound is air sensitive but less so than $(C_4H_8O)_4Mg[Co(CO)_4]_2$.

EXAMPLE H

Preparation of $(C_4H_8O)_4Mg[Co(CO)_3PCH_3(C_6H_5)_2]_2$

This compound was prepared by cleaving the cobalt-cobalt bond in $Co_2(CO)_6(CH_3P(C_6H_5)_2)_2$ with a magnesium amalgam in tetrahydrofuran solution. $Co_2(CO)_6(CH_3P(C_6H_5)_2)_2$ was prepared by allowing two equivalents of $CH_3P(C_6H_5)_2$ to react with one equivalent of $Co_2(CO)_8$ in refluxing benzene. The substitution reaction was complete in 24 hours. $(C_4H_8O)_4Mg[Co(CO)_3CH_3P(C_6H_5)_2]_2$ was obtained analytically pure by repeated recrystallizations from benzene. The pure compound is yellow. The stoichiometry of the compound was established by elemental analyses and nmr measurements.

EXAMPLE I

Preparation of $(C_5H_5N)_4Mg[Co(CO)_3PCH_3(C_6H_5)_2]_2$

This was prepared by reducing a benzene solution of $Co_2(CO)_6(PCH_3(C_6H_5)_2)_2$ with magnesium amalgam in the presence of a two-fold excess of pyridine. A light yellow, air sensitive solid was isolated by concentrating the filtered reaction mixture with reduced pressure and flooding the concentrate with n-pentane. The product was purified by recrystallizing from benzene. The yield was nearly 100%. The molecular formula was obtained by nmr measurements and elemental analyses.

EXAMPLE J

Preparation of $[(CH_3)_2NCH_2CH_2N(CH_3)_2]_2Mg[Co(CO)_3PCH_3(C_6H_5)_2]_2$ This light yellow compound was obtained in a manner very similar to that used in preparing $(C_5H_5N)_4Mg[Co(CO)_3PCH_3(C_6H_5)_2]_2$ but with tetramethylethylenediamine being substituted for pyridine. The stoichiometry of the compound was established by elemental analyses and nmr measurements.

EXAMPLE K

Preparation of $(C_4H_8O)_4Mg[Mn(CO)_2]_2$ 0.1 moles of $Mn_2(CO)_{10}$ in tetrahydrofuran was reduced with excess 1% magnesium amalgam. After 18 hours the reaction mixture was filtered and a yellow filtrate was obtained. The filtrate was concentrated with reduced pressure. The concentrate yielded a yellow solid upon addition of n-pentane. The air sensitive yellow solid was found to be only sparingly soluble in benzene. Purification was effected by washing the solid with a 50:50 benzene-n-pentane mixture to remove any unreacted $Mn_2(CO)_{10}$. The washed solid was redissolved in tetrahydrofuran, filtered and reprecipitated with n-pentane. This redissolving-reprecipitation process was repeated several times. The yield was very nearly quantitative. Elemental analysis established the compound as the tetrakis tetrahydrofuran adduct. Note that the elemental analysis (Table I) establishes that the bis-adduct is not formed, as claimed by Hieber et al. Infrared spectral studies also confirm that the tetrakis adduct is the only product formed.

EXAMPLE L

Preparation of $(C_4H_8O)_4Mg[Mn(CO)_4PCH_3(C_6H_5)_2]_2$

To a slurry of $(C_4H_8O)_4Mg(CO)_5)_2$ in toluene a two molar equivalent of $CH_3P(C_6H_5)_2$ was added and the mixture was refluxed for two hours. While concentrating the reaction mixture with reduced pressure, a yellow solid came out of solution and was collected by filtration. The stoichiometry of the phosphine derivative was established by elemental analysis and nmr spectroscopy. The addition of phosphine was nearly quantitative. The phosphine derivative has a much higher solubility in aromatic solvents than the unsubstituted compound.

EXAMPLE M

Preparation of $(C_5H_5N)_4Mg[Mn(CO)_5]_2$ 0.1 moles of $Mn_2(CO)_{10}$ in benzene containing a small stoichiometric excess of pyridine was reduced with a 1% magnesium amalgam. After 18 hours the reaction mixture was filtered yielding a light green filtrate. Solvent was removed from the filtrate until solid started to come out of solution. N-pentane was added to the concentrated solution, resulting in a nearly quantitative recovery of the desired product. The recrystallized compound is light green. The stoichiometry of the air sensitive compound was established by elemental analysis.

Use of the Novel Catalyst In the Carbonylation of Alkanols to Carboxylic Acid Esters

EXAMPLE 1—Use of Cobalt Catalyst to Obtain Methyl Acetate $(THF)_4Mg[Co(CO)_3P(C_4H_9)_3]_2+CH_3I$ catalyst system
Feed: 2.0 gm (2 mmoles)$(THF)_4Mg[Co(CO)_3P(C_4H_9)_3]_2$, 0.5 ml (8 mmoles) $CH_3I$, 30 ml methanol, 70 ml benzene.
Reaction conditions: 800 psi CO pressure, 120° C., 48 hours.
Products: 37% conversion to methyl acetate, trace amount of $CH_3OCH_3$
Note a molar ratio of cocatalyst/catalyst of 4 resulted in substantially no ether formation.

EXAMPLE 2—Carbonylation of Ethanol $(THF)_4Mg[Co(CO)_3P(C_4H_9)_3]_2+CH_3I$ catalyst system
Feed: 2.0 gm (2 mmoles)$(THF)_4Mg[Co(CO)_3P(C_4H_9)_3]_2$, 0.5 ml (8 mmoles) $CH_3I$, 100 ml ethanol.
Reaction conditions: 600 psi CO pressure, 200° C., 48 hours.
Products: 15% conversion to ethyl propionate, 6.7% conversion to ethyl ether.

EXAMPLE 3—Mixed Alcohol Carbonylation Process $(THF)_4Mg[Co(CO)_3P(C_4H_9)_3]_2+CH_3I$ catalyst systems
Feed: 0.5 gm (0.5 mmoles)$(THF)_4Mg[Co(CO)_3P(C_4H_9)_3]_2$, 0.5 ml (8 mmoles) $CH_3I$, 30 ml isopropanol, 40 ml benzene, 30 ml methanol.
Reaction conditions: 800 psi CO pressure, 185° C. 72 hours.
Products: wt. %, methanol 1, isopropanol 20, methyl acetate 15, isopropyl acetate 25, isopropyl ether 5, methyl isopropyl ether 20, methyl ether 5.

Example 3 is typical of mixed alcohol runs where unsymmetrical ethers and lower alcohol acyl esters are preferentially formed.

The following tables summarize the effects of changing the temperature, carbon monoxide pressure and cocatalysts on the ability of $(THF)_4Mg[Co(CO)_3P(C_4H_9)_3]_2$ to catalyze the carbonylation of methanol to methyl acetate.

EXAMPLE 4—The effect of Temperature on the Production of

from $CH_3OH$
Feed: 90 ml $CH_3OH$, 10 ml $C_6H_6$, 1.0 mmole $(THF)_4Mg[Co(CO)_3P(C_4H_9)_3]_2$, 8 mmoles $CH_3I$, 4000 psi Co pressure, 4 hour reaction time.

| Experiment | Temperature, °C. | ml $CH_3COCH_3$ produced |
|---|---|---|
| A | 100 | 3.5 |
| B | 150 | 21.8 |
| C | 175 | 29.6 |
| D | 200 | 14.4 |

EXAMPLE 5—The Effect of Pressure on the Production of

from $CH_3OH$
Feed: 90 ml $CH_3OH$, 10 ml $C_6H_6$, 1.0 mmole $(THF)_4Mg[Co(CO)_3P(C_4H_9)_3]_2$, 8.0 mmoles $CH_3I$, 175° C., 4 hour reaction time.

| Experiment | Pressure(psi) | ml $CH_3COCH_3$ produced |
|---|---|---|
| A | 500 | 2.0 |
| B | 1000 | 4.5 |
| C | 4000 | 29.6 |

EXAMPLE 6—The Effect of CH₃I Concentration on the Production of

from CH₃OH

Feed: 90 ml CH₃OH, 10 ml C₆H₆, 1.0 mmole (THF)₄Mg[Co(CO)₃P(C₄H₉)₃]₂, 1000 psi Co pressure, 175° C., 20 hour reaction time

| Experiment | CH₃I (mmole) | ml CH₃COCH₃ produced | ml CH₃OH consumed |
|---|---|---|---|
| A | 1.6 | 0.5 | 1.2 |
| B | 8.0 | 22.4 | 30.0 |
| C | 16.0 | 4.5 | 45.0* |
| D | 48.0 | 1.2 | 90.* |

*At high CH₃I concentration CH₃OH is dehydrated to CH₃OCH₃.

Note that at a CO pressure of 1000 psi optimum methyl acetate production begins to decline at a cocatalyst-catalyst molar ratio of more than 8 in contradistinction where lower pressures and a similar ratio produces >95% conversion to dimethyl ether. This experiment demonstrates the interdependency of the cocatalyst-catalyst ratio and CO pressure variables.

EXAMPLE 7—The Effect of Cocatalyst on the Production of

from CH₃OH

Feed: 90 ml CH₃OH, 10 ml C₆H₆, 1.0 mmole (THF)₄Mg[Co(CO)₃P(C₄H₉)₃]₂, 4000 psi CO pressure, 175° C., 4 hours reaction time

| Cocatalyst(mmole) | ml CH₃COCH₃ produced |
|---|---|
| LiI (4.0) | 1.0 |
| None | 2.0 |

| Cocatalyst(mmole) | ml CH₃COCH₃ produced |
|---|---|
| I₂ (2.0) | 5.2 |
| HI (4.0) | 6.6 |
| CH₃I (16.0) | 19.8 |
| CH₃I (8.0) | 29.6 |
| CH₃CH₂I (8.0)* | 17.5 |
| C₆H₅I (8.0)* | 22.3 |
| CH₃I (8.0)* | 21.4 |

*1000 psi CO

Note that longer reaction times were required at lower pressure to produce comparable conversion level, i.e., CH₃I., 18 hours, CH₃CH₂I..19 hours, C₆H₅I..90 hours.

EXAMPLE 8—Effect of Catalyst on the Carbonylation of Methanol to Methyl Acetate Feed: 90 ml (2.22 moles) CH₃OH, 10 ml (0.11 mole) benzene Reaction conditions: 175° C., 1000 psi

TABLE II

| Catalyst (mmole) | Cocatalyst (mmole) | Reaction Time (Hour) | % Conversion | % Selectivity[a] |
|---|---|---|---|---|
| (C₄H₈O)₄Mg[Co(CO)₃P(C₄H₉)₃]₂ (2.0) | CH₃I (8.0) | 19 | 28 | 99+[b] |
| (C₄H₈O)₄Mg[Co(CO)₃P(C₄H₉)₃]₂ (1.0) | CH₃I (8.0) | 18 | 24 | 85 |
| (C₄H₈)₄Mg(Mn(CO)₅)₂ (2.8) | CH₃I (8.0) | 19 | trace | — |
| [(C₄H₉)₃P]₃Cu—Co(CO)₃P(C₄H₉)₃ (2.0) | CH₃I (8.0) | 16 | 10 | 24 |
| NaCo(CO)₃P(C₄H₉)₃ (2.0) | CH₃I (8.0) | 19 | 5.0 | 14 |
| Co₂(CO)₆[P(C₄H₉)₃]₂ (1.0) | CH₃I (6.0) | 20 | 9.0 | 37 |
| Co₂(CO)₈ (1.0) | CH₃I (8.0) | 21 | 3.5 | 6.4 |
| Co₂(CO)₆(P(C₄H₉)₃)₂ (1.0) | CH₃I (8.0) | 19 | 3.5 | 10 |
| Co(C₅H₇O₂)₃ (2.0) | CH₃I (8.0) | 67 | 16 | 23 |

[a]Additional product was dimethyl ether
[b]No dimethyl ether was collected in the off-gases vented through a toluene bath at −80° C.

As can be seen from Table II, the magnesium cobalt carbonyls are much superior catalysts with respect to both product selectivity and catalyst activity than the other compounds tested. The low activity and product selectivity exhibited by Co₂(CO)₆(P(C₄H₉)₃)₂ strongly suggests that the novel compounds, i.e., (C₄H₈O)₂Mg[Co(CO)₃P(C₄H₉)₃]₂ complex does not decompose under reaction condition into cobalt carbonyl dimer. Since the magnesium-transition metal derivatives contain a polar metal-metal bond it was suspected that ionic compounds such as NaCo(CO)₃P(C₄H₉)₃ and [P(C₄H₉)₃]₃CuCo(CO)₃P(C₄H₉)₃ would show comparable catalytic activity. Table II clearly shows that this is not the case. Additional experimental evidence has suggested that the catalyst differences between these ionic complexes and the magnesium transition metal compounds is directly related to the relative ease of production of alkyl and hydride intermediate species generated by addition of an alkyl iodide cocatalyst.

It has been found that conversions in the range of between 20-40% are obtained in batch autoclave experiments. These results suggest that the extents of the reaction is equilibrium controlled. Recycle experiments have shown continued catalyst activity thus conversion is not limited by a short catalyst lifetime. The reaction can most likely be forced toward higher methyl acetate yields by removing water as it is formed.

The absence of detectable amounts of acetic acid in the reaction mixture by the reaction of methyl acetate with water can be explained by the fact that K (equil.) for the esterification reaction has been found to be near 16 at 175° C.

To illustrate this point in a typical carbonylation in which 2.2 moles of methanol is converted into 0.40 moles of methyl acetate only 0.0071 moles of

would be present as equilbrium. Turn over numbers (mole methanol converted/mole catalyst) as high as $10^3$ have been obtained.

It has been found that iodine containing compounds are required as cocatalysts in the carbonylation of methanol with the novel magnesium-transition metal catalysts. As an expansion on the results shown in Example 7, a list of the numerous cocatalysts tested in conjunction with $(C_4H_8O)_4Mg[Co(CO)_3P(C_4H_9)_3]_2$ are compared in Table III.

Table III suggests that the ability of a cocatalyst to promote the carbonylation of methanol to methyl acetate varies greatly with the type of iodine containing compound employed. The activity was found to decrease in the order $CH_3I \approx CH_3CH_2I > C_6H_5I > HI \approx I_2 > LiI$, thus suggesting that low chain length alkyl iodides are the preferred cocatalyts. The promotional effect of iodine is unique as Cl and Br containing compounds such as $CH_3Cl$ and $CH_3Br$ were found to be inventive. This result suggests that the carbon-halogen bond strength (C-Cl > C-Br > C-I) plays a dominant role in the primary catalyst activation step.

The first two entries in Table III suggests that the activity of $CH_3I$ is concentration dependent. This was found to be true and is expanded upon in Table IV.

TABLE III

EFFECT OF COCATALYST ON THE CARBONYLATION OF METHANOL TO METHYL ACETATE

Feed: 2.22 mole methanol
0.11 mole benzene
1.0 mmole $(C_4H_8O)_4Mg[Co(CO)_3P(C_4H_9)_3]_2$
Reaction Conditions: 175° C., 4000 psi CO

| Cocatalyst | mmole | t(hr) | % Conversion to Methyl Acetate | % Selectivity to Methyl Acetate |
|---|---|---|---|---|
| $CH_3I$ | 8.0 | 3.25 | 29 | 97 |
| $CH_3I$ | 16.0 | 4.25 | 25 | 74 |
| $I_2$ | 4.0 | 5.50 | 8 | 27 |
| LiI | 4.0 | 4.0 | 0.6 | 100 |
| HI | 4.0 | 4.25 | 8 | 47 |
| $CH_3I$[a] | 8.0 | 18 | 24 | 85 |
| $CH_3CH_2I$[a] | 8.0 | 19 | 20 | 85 |
| $C_6H_5I$[a] | 8.0 | 90 | 25 | 52 |

[a]1000 psi $CO_2$ longer reaction time required at this lower pressure to produce comparable conversion levels.

TABLE IV

EFFECT OF $CH_3I$ CONCENTRATION ON THE CARBONYLATION OF METHANOL TO METHYL ACETATE

Feed: 2.22 mole methanol
0.11 mole benzene
1.0 mmole $(C_4H_8O)_4Mg[Co(CO)_3P(C_4H_9)_3]_2$
Reaction Conditions: 175° C. 1000 psi CO

TABLE IV-continued

EFFECT OF $CH_3I$ CONCENTRATION ON THE CARBONYLATION OF METHANOL TO METHYL ACETATE

| $CH_3I$ (mmole) | t(hr) | % Conversion to Methyl Acetate | % Selectivity to Methyl Acetate |
|---|---|---|---|
| 1.6[a] | 18 | 0.0 | 0.0 |
| 4.0 | 18 | 22 | 100 |
| 6.0 | 18 | 24 | 100 |
| 8.0 | 18 | 24 | 85 |
| 12.0 | 18 | 5.4 | 15 |
| 16.0 | 18 | 4.5 | 12 |
| 48.0[b] | 17 | 0.0 | 0.0 |
| 8.0[c] | 3.25 | 29 | 97 |
| 16.0[c] | 4.25 | 25 | 74 |

[a]no reaction occurs
[b]100% conversion to $CH_3OCH_3$
[c]4000 psig. CO employed Table IV shows the optimum conversion and selectivity to methyl acetate occurs when the cocatalyst to catalyst ratio is between 4-8 to 1. When this ratio is much less than 4 or much greater than 8 either no carbonylation occurs at all or complete dehydration to dimethyl ether takes place. At higher pressures (4000 psig CO) the concentration effect is not as pronounced. This effect is demonstrated by the last two entries in Table IV.

It has been found that the rates of carbonylation become progressively slower as the chain length of the alcohol increases. The seletivity to ester products was also found to decrease in the same direction. Secondary alcohols such as isopropyl alcohol presents the problem of dehydration to olefins. This dehydration can be eliminated by operating at lower reaction temperatures, i.e., 150° C.

A catalyst system analogous to the catalyst system described in Example 10 of U.S. Pat. No. 3,769,329 to Paulik et al was prepared and it was compared with the catalyst system of the present invention. Specifically, Examples 9 and 10 below demonstrate that a catalyst system comprised of a mixture of components equivalent on a molar basis to a discrete magnesium-transition metal complex of the present invention is not equivalent and in fact is demonstrated as being an inferior catalyst system to the catalyst system of the present invention.

EXAMPLE 9

A solution was prepared by adding the following materials (composite catalyst system) to a feed solution consisting of 90 ml. of methanol and 10 ml. of benzene.

Composite Catalyst System 0.53 g. $RhCl_3 \cdot 3H_2O$ (2.0 mmoles)
1.1 g. $MgI_2$ (4.0 mmole)
1.05 g. $(C_6H_5)_3P$ (4.0 mmole)
0.15 g. $C_4H_8O$ (2.0 mmole)

The solution containing the feed and composite catalyst system were heated to 175° C. at 800 psig CO pressure for 16 hours. The products from this carbonylation reaction were analyzed to be as follows:

| Methanol conversion | — | 59% |
|---|---|---|
| Product Selectivities: | | |
| Methyl Acetate | — | 7% |
| Dimethylether | — | 93% |

When the autoclave was opened, a rhodium mirror had formed on the wall of the glass autoclave liner. This is indicative of the fact that the composite catalyst system is not stable under the above reaction conditions. The existence of this rhodium mirror also demonstrates that a discrete Mg-Rh complex is not prepared in situ.

EXAMPLE 10

The following discrete catalyst system was added to the same reactive feed as shown in Example 9, i.e., 90 ml. methanol and 10 ml. benzene.

Catalyst System:

1.0 gm (0.65 mmole) $(C_4H_8O)_2Mg[Rh(CO)_2(P(C_6H_5)_3)_2]_2$
0.5 ml (8.0 mmole) $CH_3I$ The solution containing the reactive feed and the discrete catalyst system were reacted at a temperature of 175° C. at 800 psig CO pressure for 16 hours. The products from this carbonylation reaction were analyzed to be as follows:

| | | |
|---|---|---|
| Methanol conversion | — | 79% |
| Product selectivities: | | |
| Methyl Acetate | — | 42% |
| Dimethylether | — | 58% |

Under the above conditions, the catalyst of the present invention was found to be stable, as no rhodium mirror was observed to occur on the wall of the glass autoclave liner.

Examples 9 and 10 clearly demonstrate that the catalyst system of the present invention is superior to a composite catalyst prepared on an equimolar basis. The activity and selectivity advantage exhibited by the catalyst system of the present invention is even more apparent when it is noted that the concentration of rhodium employed in Example 10 is only 65% as great as that used in the composite system (Example 9). Also, the selectivity of methyl acetate produced by the catalyst system disclosed in Example 10 is greatly improved when the $CH_3I$/catalyst ratio is lowered from the value of 12 employed in Example 10.

Other Reactions Using the Novel Catalyst Compounds
Hydroformylation

EXAMPLE 11

Hydroformylation of Propylene $(C_4H_8O)_2Mg[Rh(CO)_2(P(C_6H_5)_3)_2]_2$ has been found to be a very active hydroformylation catalyst when compared to a conventional rhodium hydroformylation catalyst such as $((C_6H_5)_3P)_2Rh(CO)Cl$ (see Table).

The reaction products are strictly butyraldehydes.
Reaction Conditions: 1000 psig Total pressure, $CO/H_2$ (50/50) mixture), 60 ml benzene as solvent, 0.30–0.45 moles propylene, 0.5 mmoles catalyst (based on Rh).

| Catalyst | T°C. | (%)n-$C_4H_8O^{(a)}$ | k min$^{-1(b)}$ | $t_{\frac{1}{2}}$ (min)$^{(c)}$ |
|---|---|---|---|---|
| $((C_6H_5)_3P)_2Rh(CO)Cl$ | 133 | 56 | 0.0744 | 9.32 |
| $(C_4H_8O)_2Mg[Rh(CO)_2(P(C_6H_5))_2]_2$ | 95 | 61 | 0.168 | 4.13 |

$^{(a)}$% n-$C_4H_8$ = percent straight chain isomer, determined by G.C. analysis.
$^{(b)}$k = pseudo 1st order reaction rate constant.
$^{(c)}t_{\frac{1}{2}}$ = ln 2/k.

The table clearly shows that the $(C_4H_8O)_2Mg[Rh(CO)_2(P(C_6H_5)_3)_2]_2$ complex is more than twice as active as $((C_6H_5)_3P)_2Rh(CO)Cl$ even at a reaction temperature nearly 40° C. lower.

EXAMPLE 12

Hydroformylation of Hexene-1

30 ml. of hexene-1, 20 ml. of benzene, and 0.3 gm. $[C_4H_8O]_4Mg[Co(CO)_3PCH_3(C_6H_5)_2]_2$ were placed in a rocker bomb and pressurized to 1500 psi with a 1:1 ratio of $H_2$:CO. The bomb was heated to 140° C. and held until the reaction was complete. Analysis indicated that 99% of the hexene-1 was converted to $C_7$ aldehydes and $C_7$ alcohols. 87% of the reacted product was an aldehyde.

EXAMPLE 13

Trimerization of Butadiene 0.5 gm. $(C_4H_8O)_4Mg[Ni(CO)C_5H_5]_2$ and 5 ml. of benzene were placed in a small (ca. 50 ml.) pressure reactor under a nitrogen atmosphere. To the catalyst was condensed 15 ml. of butadiene after passage through a drying train of $CaH_2$ and KOH. This mixture was warmed to 60° C. The resulting pressure was ca. 65 psi. The mixture was allowed to stir under these conditions for 2½ hours, after which the pressure had dropped to less than 5 psi.

A gas chromatographic analysis of the reaction mixture showed essentially complete conversion of butadiene into the following cyclic oligomers:

| Oligomer | % (wt.) |
|---|---|
| vinyl cyclohexene | 7.6 |
| 1,5-cyclooctadiene | 9.9 |
| trans,trans,trans,1,5,9-cyclododecatriene | 78.5 |
| cis,trans,trans,1,5,9-cyclododecatriene | 4.0 |

This result is in contrast to the product distribution obtained when $(Ni(CO)C_5H_5)_2$, the precursor complex in the preparation of $(C_4H_8O)_4Mg[Ni(CO)C_5H_5]_2$, is employed as a catalyst. In the latter case, the primary products are dimers (see table below).

| Oligomer | % (weight) |
|---|---|
| vinyl cyclohexene | 69 |
| 1,5-cyclooctadiene | 27 |
| trans,trans,trans,1,5,9-cyclododecatriene | 4 |

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention.

What is claimed is:
1. A catalyst composition comprising a mixture of:
 (A) a compound selected from the group consisting of:
 $(C_4H_8O)_4Mg[Co(CO)_3P(C_4H_9)_3]_2$ and
 $(C_4H_8O)_2Mg[Rh(CO)_2(P(C_6H_5)_3)_2]_2$.
2. The composition of claim 1 wherein the organo iodine compound is $CH_3I$.

* * * * *